US008043234B2

United States Patent
Talish et al.

(10) Patent No.: US 8,043,234 B2
(45) Date of Patent: *Oct. 25, 2011

(54) SYSTEM AND METHOD FOR PROVIDING THERAPEUTIC TREATMENT USING A COMBINATION OF ULTRASOUND, ELECTRO-STIMULATION AND VIBRATIONAL STIMULATION

(75) Inventors: Roger J. Talish, Hillsborough, NJ (US); Clinton T. Rubin, Port Jefferson, NY (US); Kenneth J. McLeod, Vestal, NY (US)

(73) Assignee: American Medical Innovations, L.L.C., Fort Myers, FL (US)

( * ) Notice: Subject to any disclaimer, the term of this patent is extended or adjusted under 35 U.S.C. 154(b) by 701 days.

This patent is subject to a terminal disclaimer.

(21) Appl. No.: 11/716,519

(22) Filed: Mar. 8, 2007

(65) Prior Publication Data

US 2007/0219470 A1 Sep. 20, 2007

Related U.S. Application Data

(60) Provisional application No. 60/873,327, filed on Dec. 7, 2006, provisional application No. 60/780,336, filed on Mar. 8, 2006.

(51) Int. Cl.
*A61N 7/00* (2006.01)
(52) U.S. Cl. .......................................................... 601/2
(58) Field of Classification Search ........................ 601/2
See application file for complete search history.

(56) References Cited

U.S. PATENT DOCUMENTS

| | | | |
|---|---|---|---|
| 4,013,069 A | 3/1977 | Hasty | |
| 4,530,360 A | 7/1985 | Duarte | |
| 4,858,599 A | 8/1989 | Halpern | |
| 5,003,965 A | 4/1991 | Talish et al. | |
| 5,046,484 A | 9/1991 | Bassett et al. | |
| 5,103,806 A | 4/1992 | McLeod et al. | |
| 5,145,027 A | 9/1992 | Petzl et al. | |
| 5,186,162 A | 2/1993 | Talish et al. | |
| 5,191,880 A * | 3/1993 | McLeod et al. | 601/2 |
| 5,211,160 A | 5/1993 | Talish et al. | |
| 5,273,028 A | 12/1993 | McLeod et al. | |
| 5,376,065 A | 12/1994 | McLeod et al. | |
| 5,437,668 A | 8/1995 | Aronson et al. | |
| 5,520,612 A | 5/1996 | Winder et al. | |
| 5,538,489 A | 7/1996 | Magid | |

(Continued)

FOREIGN PATENT DOCUMENTS

EP 0 029 298 A1 5/1981

(Continued)

OTHER PUBLICATIONS

PCT Notification of Transmittal of the International Search Report and The Written Opinion of the International Searching Authority for PCT/US2007/005794, dated Aug. 30, 2007.

(Continued)

*Primary Examiner* — Tse Chen
*Assistant Examiner* — Hien Nguyen
(74) *Attorney, Agent, or Firm* — Malloy & Malloy, P.A.

(57) ABSTRACT

Systems and methods are disclosed for providing therapeutic treatment using vibrational stimulation, ultrasound stimulation and electro-stimulation. The combined therapeutic treatment allows for more flexible and effective treatment of bone-loss related and other ailments and conditions by providing one or a combination of vibrational, ultrasound and/or electro-stimulation to a patient.

2 Claims, 6 Drawing Sheets

U.S. PATENT DOCUMENTS

| | | | |
|---|---|---|---|
| 5,556,372 | A | 9/1996 | Talish et al. |
| 5,730,705 | A | 3/1998 | Talish et al. |
| 5,762,616 | A | 6/1998 | Talish |
| 5,904,659 | A * | 5/1999 | Duarte et al. ............... 601/2 |
| 5,971,984 | A | 10/1999 | Taylor et al. |
| 5,997,490 | A | 12/1999 | McLeod et al. |
| 6,050,364 | A | 4/2000 | Popall et al. |
| 6,234,975 | B1 | 5/2001 | McLeod et al. |
| 6,440,046 | B1 | 8/2002 | Tholkes |
| 6,558,304 | B1 | 5/2003 | Bardon et al. |
| 6,561,991 | B2 | 5/2003 | McLeod et al. |
| 6,607,497 | B2 | 8/2003 | McLeod et al. |
| 6,610,021 | B1 | 8/2003 | Bock |
| 6,620,117 | B1 | 9/2003 | Johnson et al. |
| 6,843,776 | B2 | 1/2005 | Trandafir et al. |
| 6,884,227 | B2 | 4/2005 | Krompasick |
| 6,902,320 | B2 | 6/2005 | McKenna |
| 2003/0090374 | A1 * | 5/2003 | Quigley ............... 340/506 |
| 2004/0059331 | A1 | 3/2004 | Mullaney |
| 2004/0260211 | A1 * | 12/2004 | Maalouf ............... 601/15 |
| 2005/0148911 | A1 | 7/2005 | Talish et al. |
| 2005/0193820 | A1 * | 9/2005 | Sheljaskow et al. ........... 73/649 |
| 2005/0251068 | A1 | 11/2005 | Mor |
| 2006/0047230 | A1 | 3/2006 | Talish |
| 2007/0232963 | A1 * | 10/2007 | Talish et al. ............... 601/2 |

FOREIGN PATENT DOCUMENTS

| | | |
|---|---|---|
| EP | 1 656 921 A1 | 5/2006 |
| WO | WO 95/21580 | 8/1995 |
| WO | WO 02/053084 A1 | 7/2002 |
| WO | WO 2006/096662 A1 | 9/2006 |
| WO | WO 2006/096734 A1 | 9/2006 |

OTHER PUBLICATIONS

PCT Notification of Transmittal of the International Search Report and the Written Opinion of the International Searching Authority for PCT/US2007/005792, dated Sep. 9, 2008.

Walsh, W.R. et al., Influence of Dynamic Motion Therapy on bone ingrowth into a bone graft substitute, Surg. & Ortho. Research Labs., Univ. of New S. Wales, Australia.

Bassett, C. et al., Generation of Electric Potentials by Bone in Response to Mechanical Stress, Science Magazine, Sep. 28, 1962, pp. 1063-1064, 137.

Pope, M.H. et al., "Mounting of the Transducers in Measurement of Segmental Motion of the Spine," J. Biomechanics, 1986, pp. 675-677, vol. 19, No. 8.

Holmlund et al., "Mechanical impedance of the human body in vertical direction," Applied Ergonomics, Elsevier Science Ltd. (2000).

Jordan, J., "Good Vibrations and Strong Bones," Am. J. Physiol. Reful. Integr. Comp. Physiol., 288 (3): R555-556 (2005).

Stewart, J.M. et al., "Plantar vibration improved leg fluid . . . ," The American Journal of Phgy—Reg, Integ and Comp Phgy, Oct. 7, 2004, 288:R623-R629, New York, NY.

Midura, R.J. et al., "Low amplitude, high frequency strains imposed . . . ," Medical Engineering & Physics, Mar. 9, 2005, pp. 285-293, vol. 27, Issue4, Elsevier Inc., Chicago, IL.

* cited by examiner

SYSTEM AND METHOD FOR PROVIDING THERAPEUTIC TREATMENT USING A COMBINATION OF ULTRASOUND, ELECTRO-STIMULATION AND VIBRATIONAL STIMULATION

PRIORITY

The present application claims priority from U.S. Provisional Application Ser. No. 60/873,327, entitled "Non-Invasive Apparatuses And Methods For Vibrational Treatment Of Bone Tissue Following A Bone-Related Medical Procedure," filed on Dec. 7, 2006; the present application also claims priority from U.S. Provisional Application Ser. No. 60/780,336, entitled "System and Method for Providing Therapeutic Treatment Using a Combination of Ultrasound, Electro-Stimulation and Dynamic Motion Therapy," filed on Mar. 8, 2006. The entire contents of both applications are incorporated herein by reference.

CROSS-REFERENCE TO RELATED APPLICATIONS

This application is related to United States and PCT patent application filed on Mar. 8, 2007 both entitled "System and Method for Providing Therapeutic Treatment Using a Combination of Ultrasound and Vibrational Stimulation" by Talish et al. The entire contents of these applications are incorporated herein by reference.

BACKGROUND

1. Technical Field

The present disclosure relates generally to therapeutic treatment. In particular, the present disclosure relates to a therapeutic treatment using a combination of ultrasound, electro-stimulation and vibrational stimulation for the treatment of the musculoskeletal system.

2. Description of the Prior Art

Weakened bone structure and improperly healed or slowly healing bone fractures may result in reduced quality of life. Quality of life may be improved for patients with bone fractures by ensuring rapid healing and by inhibiting the loss of bone mineral content (bone mass), and therefore bone strength, associated with fractures. Metabolic bone diseases, such as osteoporosis, also reduce the quality of life.

Osteoporosis is a pernicious disorder usually, but not exclusively, afflicting elderly women. The osteoporotic state can also be manifested by those who are confined to a bed and even to astronauts who are subjected to prolonged weightlessness. Osteoporosis occurs through a decrease in bone mass, which makes the afflicted bones more fragile and more susceptible to breakage.

The reduction in bone mass from osteoporosis results when destruction outpaces bone formation. The balance between destruction and formation is affected by hormones, calcium intake, vitamin D and its metabolites, weight, smoking, alcohol consumption, age, genetic determinants and especially exercise or other methods of dynamically loading the bone tissue as well as many other factors. Considering the vast array of factors which can compromise the healing process, any form of stimulation that can accelerate, augment and/or ensure the healing process are greatly needed.

Osteoporosis is not easily determined in its early phases as physical deformity is not yet evident. Because osteoporosis develops progressively, early diagnosis and appropriate treatment may avoid a serious condition. Appropriate diet and exercise can be used in early years to prevent the damaging effects of osteoporosis later in life.

Besides the nutritional and genetic causes of osteoporosis, bone loss also occurs from prolonged exposure to weightless environments, i.e., prolonged periods in space as experienced by the crews of the International Space Station. When these crews return to the normal gravity of Earth, there bone loss could make them more susceptible to fractures. The longer the duration of weightlessness experienced by an astronaut, the greater the resulting bone loss and, consequently, the greater the risk of injury or immobilization. Various techniques have been employed to minimize the impact of prolonged weightlessness with varying degrees of success.

Methods and apparatus for maintaining or promoting bone growth are described in numerous patents. For example, McLeod et al., U.S. Pat. Nos. 5,103,806, 5,191,880, 5,273,028, 5,376,065, 6,234,975, 6,561,991 B2 and 6,607,497 B2 all incorporated herein by reference, collectively describe means and methods for promoting bone growth and preventing bone loss. The method described in the above-referenced patents relates to a mechanical vibrational loading of bones to promote growth in a non-invasive procedure.

Mechanical loading on bone tissue at strains of between about 0.5 to about 500 microstrain and induced within a predetermined frequency range can prevent bone loss and enhance new bone formation. Such mechanical bone loading of tissue may be introduced by various systems, including vibrating floor plates and chairs such as ones used for the generation of resonant vibrations, electrical stimulation of muscles, isometric exercises, modulated ultrasound or transducers attached to the skin or external fixation devices to focus energy to the fracture site.

A method of using resonant vibrations for treating postural instability is described in U.S. Pat. No. 6,607,497 B2. The method includes the steps of (a) providing a vibration table having a non-rigidly supported platform; (b) permitting the patient to rest on the non-rigidly supported platform for a predetermined period of time; and (c) repeating the steps (a) and (b) over a predetermined treatment duration. Step (b) includes the steps of (b1) measuring a vibrational response of the patient's musculoskeletal system using a vibration measurement device; (b2) performing a frequency decomposition of the vibrational response to quantify the vibrational response into specific vibrational spectra; and (b3) analyzing the vibrational spectra to evaluate at least postural stability.

The method described in U.S. Pat. No. 6,607,497 B2 entails the patient standing on the vibration table or unstable standing platform, which includes at least one accelerometer mounted to the outboard side thereof. The patient is then exposed to a vibrational stimulus by the unstable standing platform. The unstable standing platform causes a vibrational perturbation of the patient's neurosensory control system. The vibrational perturbation causes signals to be generated within at least one of the patient's muscles to create a measurable response from the musculoskeletal system. These steps are repeated over a predetermined treatment duration for approximately ten minutes a day in an effort to improve the postural stability of the patient.

SUMMARY

The present disclosure describes combined therapeutic treatment systems and methods for providing multiple therapeutic treatments of bone-loss related ailments. A specific combined therapeutic treatment system includes a vibrating plate therapeutic treatment system having a supporting base and a platform dimensioned to fit in juxtaposed alignment with the base, an electro-stimulation therapeutic treatment system, and an ultrasound therapeutic treatment system. The electro-stimulation and ultrasound therapeutic treatment systems are configured to operate either alone or in conjunction with the vibrating plate therapeutic treatment system.

In addition, a controller in electrical communication with the vibrating plate, electro-stimulation and ultrasound therapeutic treatment systems is included in the disclosed combined therapeutic system. The controller is configured to provide operational signals to the therapeutic treatment systems and monitor feedback to an operator.

A specific method in accordance with the present disclosure applies a vibrational stimulation to a targeted body region, along with an electro-stimulation and/or an ultrasound stimulation. Operational parameters of the applied stimulations are controllable by monitoring patient response to the applied stimulations, and the effectiveness of the therapeutic treatment is evaluated based on the monitored response. The operational parameters and treatment duration may be adjusted, as needed, to provide a desired therapeutic result.

DESCRIPTION OF THE PREFERRED EMBODIMENTS

Detailed embodiments of the present disclosure are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Some of the therapeutic benefits of Dynamic Motion Therapy are that it prevents and reverses the loss of muscle and bone tissue (these are two characteristics of osteoporosis), it reduces the possibility of spinal or hip fractures, it is an excellent option for those unable or unwilling to take osteoporosis medication, it is noninvasive and less costly than chronic drug therapy, it is gentle in its repetitive vertical movement, it is convenient with a daily treatment of less than 1 hour and preferably about 10 to 20 minutes, and it is simple, mobile and safe to use.

Furthermore, because the present disclosure incorporates the known beneficial effects of ultrasound therapy with Dynamic Motion Therapy, therapeutic benefits, not found when either system is used separately, can be attained. The combination of vibrational and ultrasound stimulation can massage soft tissues effortlessly, and in most cases, painlessly. In addition, the systems and methods in accordance with the present disclosure help alleviate muscle spasms and reduce inflammation and swelling. Also, the systems and methods in accordance with the present disclosure improve range of motion, help increase blood flow and interstitial fluid flow, promote bone growth, and decrease pain and stiffness.

Combined Ultrasound and Vibrational Therapeutic Treatment System

Figure 1:
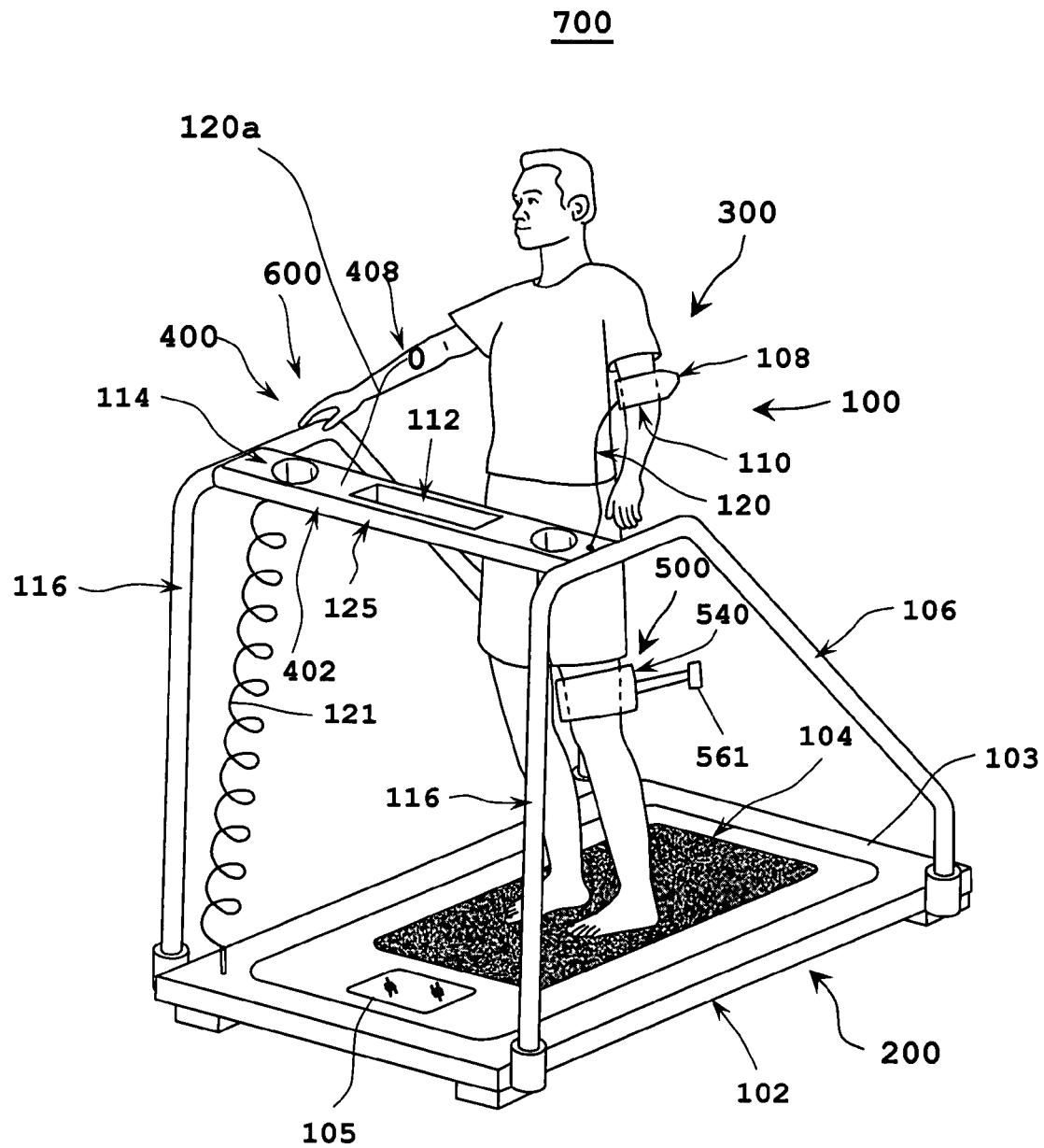
FIG. 1 is a perspective view of a system for providing combined vibrational and ultrasound stimulation, combined vibrational and electro-stimulation and/or combined vibrational, ultrasound and electro-stimulation in accordance with the present disclosure.

Referring to FIG. 1, the present disclosure provides a combined ultrasound and vibrational treatment (UVT) system 100 for providing therapeutic treatment using a combination of ultrasound and vibrational stimulation. The UVT system 100 incorporates a first therapeutic treatment system or Dynamic Motion Therapy system 200 having a vibrational assembly 102. The UVT system 100 further includes a second therapeutic treatment system 300 having an ultrasound transducer assembly 110; both assemblies 102, 110 are controlled by receiving signals from a unified controller 112 (hereinafter referred to simply as controller 112). The controller 112 includes a power supply for powering the assemblies 102, 110. Alternatively, each assembly is controlled by its own controller and/or power supply. It is to be understood that the ultrasound transducer assembly 110 generates and transmits the ultrasound waves to the injured area of the patient.

A vibrational assembly that can be implemented with the present disclosure can be the assembly described in International Patent Application WO 2006/096734 A1, Talish et al., filed on Mar. 7, 2006, the contents of which are hereby incorporated by reference. Another type of vibrational assembly that can be implemented with the present disclosure can be the assembly described in International Patent Application WO 2006/096662 A1, also by Talish et al., filed on Mar. 6, 2006, the contents of which are hereby incorporated by reference.

Drawing one's attention again to FIG. 1, an exemplary vibrational assembly 102 of the present disclosure includes a base 103 dimensioned to support and comfortably accommodate a patient in a standing position. The base 103 non-rigidly supports a vibrational platform 104 of the vibrational assembly 102, configured to impart or apply resonant vibrations to the musculoskeletal system of a patient's body. The vibrational assembly 102 generates resonant vibrations (Step 1a in FIG. 2A) having a frequency in the range of between 1 to 10 kHz. The resonant vibrations cause a vibrational stimulation. The vibrational stimulation is applied to the patient being supported by the platform 104 (Step 2a of FIG. 2A).

For patient stability and comfort, handrails 106 are provided; allowing the patient to easily remain in a proper posture and maintain balance while the vibration treatment is being administered. Additionally, a standing harness may be provided, aiding patients unable to stand on their own to maintain proper posture. The vibrational assembly 102 further includes a display 105 for displaying data, such as treatment data.

As mentioned above, the UVT system 100 also includes a second therapeutic treatment system 300 that has the ultrasound transducer assembly 110 for facilitating bone fracture healing and/or bone/soft tissue treatment, such as treating joint and muscle sprains, bursitis, tendonitis, and the like. The UVT system 100 can include numerous types of ultrasound transducer assemblies. Some, for example, can include those as disclosed in the patents listed above and issued to Duarte and Talish et al.

The ultrasound transducer assembly 110 during treatment is actuated to generate ultrasonic waves. The ultrasonic waves cause ultrasound stimulation. The ultrasound stimulation is applied to the patient supported by the platform (Step 3a of FIG. 2A). The controller 112 controls the operational parameters of the UVT system 100 based on received signals from sensors positioned on the patient and/or within the ultrasound transducer assembly 110 (Step 4a of FIG. 2A). By controlling the operational parameters, such as amplitude and frequency of the resonant vibrations and/or ultrasonic waves, the level or intensity of the vibrational and/or ultrasonic stimulations is changed.

Figure 2A:
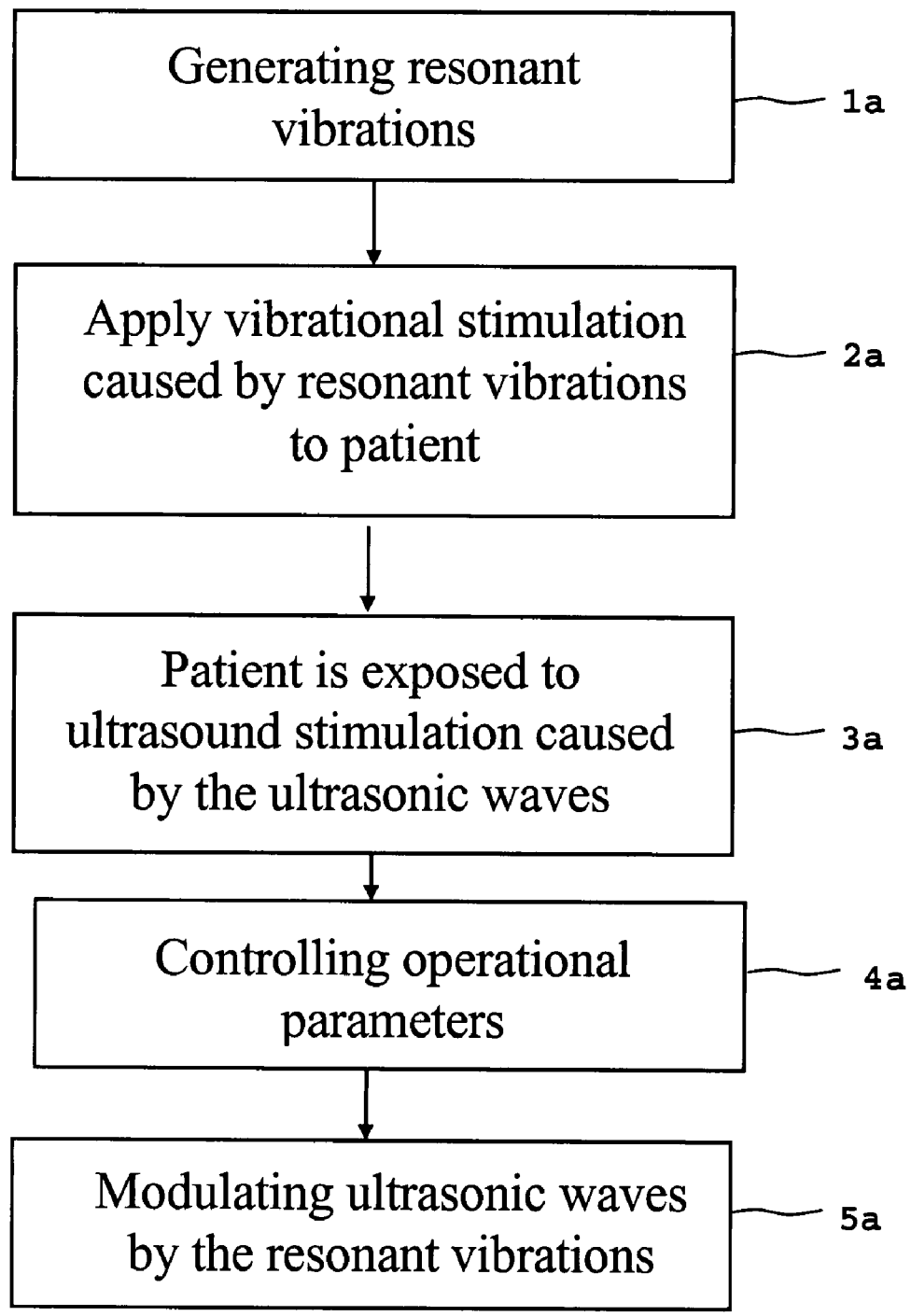
FIG. 2A is a flow chart illustrating an exemplary method for providing combined vibrational and ultrasound stimulation in accordance with the present disclosure.

One of the key features of the present disclosure is that the resonant vibrations generated by the vibrational assembly 102 modulate the continuous ultrasonic waves generated by the ultrasound transducer assembly 110 (Step 5a of FIG. 2A). For example, during treatment, the ultrasound transducer assembly 110 is placed on a patient, such that the transducer head of the assembly 110 is positioned in proximity to a bone breakage, such as a hairline fracture (e.g., less than a mm wide).

Upon actuation of the ultrasound transducer assembly 110, an ultrasound signal (carrier signal) is generated having a frequency in the range of 1-3 MHz, for example, a frequency of 1.5 MHz, and directed by the transducer head towards the hairline fracture. If the patient is standing on the vibrational platform 104 of the vibrational assembly 102 which has been actuated to generate resonant vibrations having a frequency in the range of 1-10 kHz, the bone having the hairline fracture or breakage vibrates at the same frequency as the resonant vibrations. This causes the ultrasound signal or waves within the hairline fracture to be modulated, thereby producing or setting up a modulated shear wave within the hairline fracture due to the cavitation effect. The shear wave can be a standing wave which facilitates the stimulation of bone tissue growth, thereby effectively accelerating the healing of the hairline fracture.

The above-referenced embodiments, as hereinbefore disclosed, provide for using an ultrasound transducer assembly 110 which generates ultrasonic waves having frequencies in the range of 1-3 MHz. It is envisioned that the ultrasound transducer assembly 110 can generate ultrasonic waves having low frequencies, that is, 20-100 kHz. If the ultrasound transducer assembly of the present disclosure, is operated to generate ultrasonic waves having low frequencies, it can be used for wound debridement and bacterial removal, which further promote wound and bone fracture healing.

Figure 3:
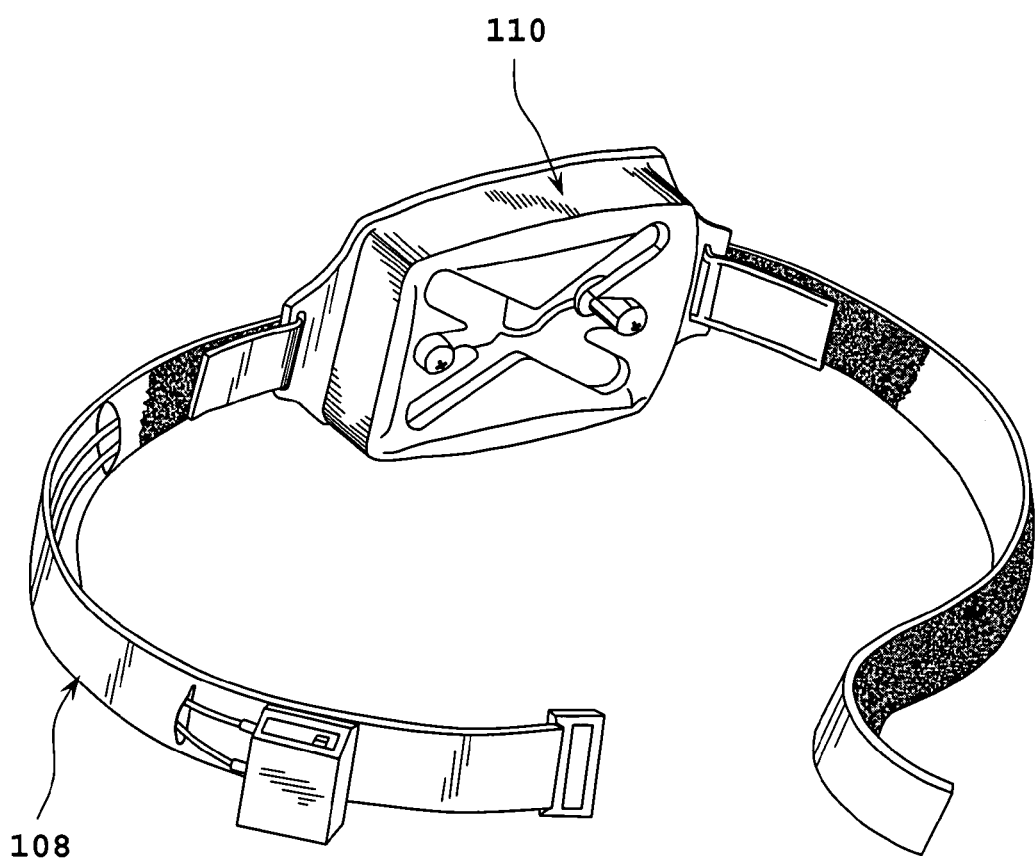
FIG. 3 is a perspective view of an ultrasound transducer assembly in accordance with the present disclosure.

With reference to FIG. 3, one embodiment of the ultrasound transducer assembly 110 is equipped with a cuff 108 capable of being fastened to the patient's body, e.g., leg, arm. The cuff 108 contains an embedded ultrasound transducer (not shown) for delivering ultrasound energy to the treatment area. Multiple ultrasound transducers may be embedded within the cuff 108 to provide multiple ultrasound energy radiating from a plurality of positions and angles. Each ultrasound transducer may be individually controllable by the controller 112. Additional cuffs 108 may be made available to allow for treatment of multiple locations, such that, for example, both legs, and the thigh and calf areas of the same leg may be treated at the same time.

The therapeutic treatment systems are, preferably, individually controllable such that a variety of treatment regimens may be devised. Additionally, a course of treatment may require alternating between the two therapeutic treatment systems for periods of time throughout the duration of a treatment session. For example, the vibrational assembly 102 may be operated for the full treatment session while the ultrasound transducer assembly 110 is operated for 10-second periods during the treatment session. As a second example, the vibrational assembly 102 is operated for 20 minutes followed by operation of the ultrasound transducer assembly 110 for 30 minutes. These are just two examples of the endless variations of timing sequences that are possible using the UVT system 100 of the present disclosure. The treatment session can be at least 10 minutes per day. The duration of the treatment can be 2-4 weeks.

Other treatment scenarios include having one or both assemblies (vibrational and ultrasound assemblies 102 and 110) operational or active during at least a portion of the treatment session, but at least one of the assemblies' operating parameters are adjusted manually or automatically during the treatment session or a portion thereof. The operating parameters can be adjusted independently of the other assemblies' operating parameters, or adjusted dependently, i.e., in accordance with, with changes in the operating parameter(s) of the other system. Additionally, the assemblies of the present disclosure can be designed wherein an operating parameter of the first therapeutic treatment system changes in accordance with a change in an operating parameter of the second therapeutic treatment system. For example, during the treatment duration, the frequency of the vibrational assembly 102 can be increased by 5 Hz for each increase in the power output of the ultrasound transducer assembly 110 of more than a predetermined wattage value. Therefore, an increase in the frequency of the vibrational assembly 102 depends on an increase in the power output of the ultrasound transducer assembly 110.

As mentioned above, the first and second therapeutic treatment systems are controlled via the controller 112. In a preferred embodiment, controller 112 can be housed in front member 114. Member 114 can be of any suitable shape known in the available art. In addition, member 114 can have a plethora of different features. For example, member 114 can have a diagnostic panel that displays different operating parameters of the ultrasound transducer assembly 110. Also, member 114 can have another diagnostic panel that displays different operating parameters of assembly 102. Member 114 can also be equipped with heart-rate displays, pulse-rate displays, calorie counter displays, fans and the like. These features can be added or removed as needed. Furthermore, located on member 114 can be control switches, buttons and the like used for controlling both the ultrasound transducer assembly 110 and the vibrational assembly 102. Controller 112 can be connected to the ultrasound transducer assembly 110 via a cable 120, as seen in FIG. 1. In an alternative embodiment, controller 112 can control ultrasound transducer assembly 110 remotely.

Additionally, the controller 112 can be operatively and selectively connected to the vibrational assembly 102. In one embodiment, the controller 112 can control vibrational assembly 102 remotely. Or, in an alternative embodiment, as seen in FIG. 1, a cable 121 can be used. If the latter embodiment is employed, that is, a cable is used, the cable can be threaded through either of support bars 116. In this embodiment, cable 121 can extend from a bottom surface 125 of member 114 to the top surface 104. The cable connections described herein are for illustrative purposes only, and by no means should be considered exhaustive of the many different connections available. Therefore, any suitable connection means known in the available art, or those connection means not yet discovered can be implemented with the present disclosure.

Figure 4:
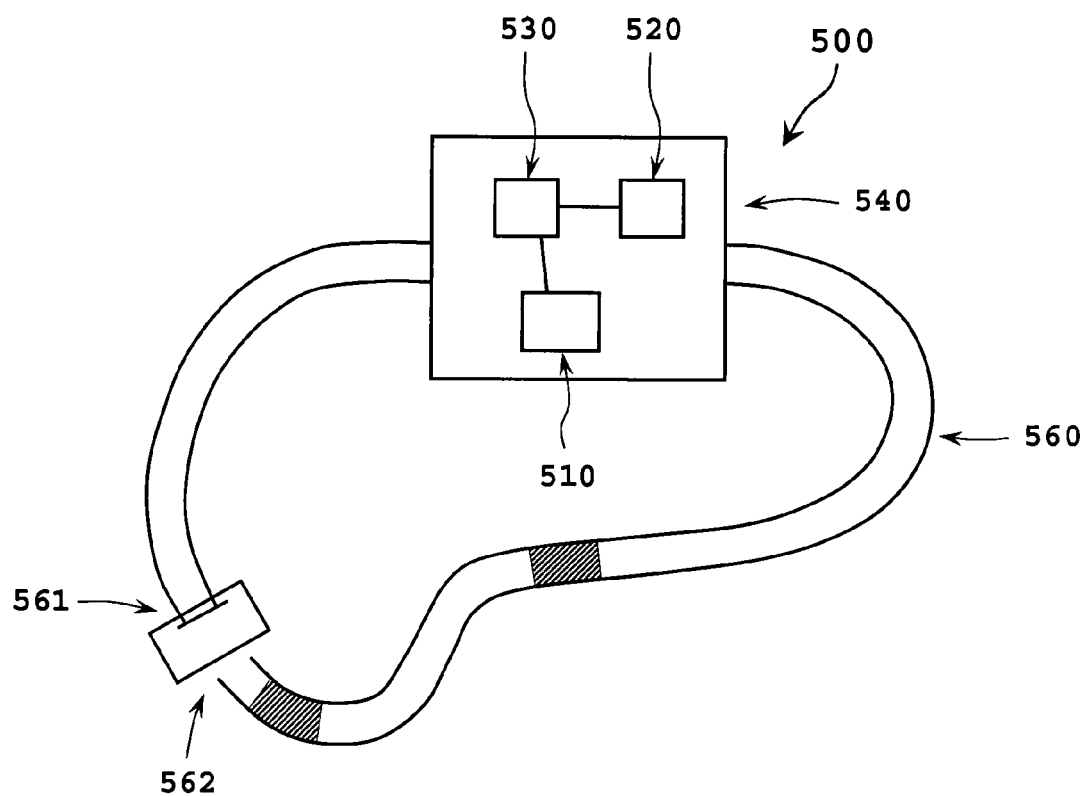
FIG. 4 is an alternative, partial perspective view of an ultrasound transducer assembly in accordance with the present disclosure.

With reference to FIG. 4, there is shown an alternative embodiment for an ultrasound transducer assembly in accordance with the present disclosure. The assembly 500 includes an ultrasound transducer 510, a power source 520, and an actuation controller 530. These components are housed within a housing 540. The actuation controller 130 is a motion sensor, such as a gravity switch or an accelerometer. The assembly 500 further includes a strap 560 having a first end 561 and a second end 562 capable of connecting to each other for strapping the assembly 500 to a patient.

Combined Electro-Stimulation and Vibrational Therapeutic Treatment System

In addition to combining system 300 with DMT system 200, the present disclosure also combines an electro-stimulation therapeutic treatment system 400 having an electro-stimulation assembly 402 with DMT system 200. In this embodiment, the patient receives the known beneficial effects of electro-stimulation therapy, as well as the beneficial effects of Dynamic Motion Therapy. The combination of vibrational and electro-stimulation can facilitate ETR or Enhanced Tissue Repair, can improve muscle tone, can increase circulation and can stimulate the skin's collagen-elastin production.

In addition, as mentioned above, the systems and methods in accordance with the present disclosure help alleviate muscle spasms and reduce inflammation and swelling. Also, the systems and methods in accordance with the improve range of motion, help increase blood flow and interstitial fluid flow, promote bone growth, and decrease pain and stiffness.

A brief discussion of electro-stimulation technology and three conventional types of electrical modalities devices that can be employed with electro-stimulation assembly 402 and DMT system 200 of the present disclosure follows below.

It is known that various cells in the body are influenced by electricity; these cells can include fibroblasts, macrophages, neutrophils and erythrocytes, along with bone, cartilage, ligaments, tendons and the like. Electro-stimulation reproduces the processes involved in muscle contraction under the control of our brain. In general, when one decides to contract a muscle, the brain sends the order in the form of electrical currents. These electrical currents travel at high speeds along the nerve fibers of the body. Once the electrical currents reach their destination, these electrical currents excite the motor nerve, which, in turn, passes the information to the immediate surroundings of the muscle, triggering a muscle contraction.

With electro-stimulation, the excitation is directly produced at the motor nerve by means of 'optimal' electrical impulses. Since the muscle cannot distinguish between a voluntary contraction (caused by the brain) and an electrically induced contraction, the work that the muscle produces is the same irrespective of the nature of the order.

Several different electro-stimulation assemblies exist, each producing different frequencies, waveforms, and effects. Electro-stimulation assemblies can employ the followng electrical modalities, they can include: Transcutaneous Electrical Nerve Stimulation (hereinafter "TENS") (the most commonly used); Interferential Current (hereinafter "IFC"); and Galvanic Stimulation (hereinafter "GS"). Each of these electrical modalities can be employed with electro-stimulation system 400 of the present disclosure. As a result, a brief discussion of each of the electrical modalities and how they are employed with electro-stimulation system 400 of the present disclosure follows.

GS, also known as galvanic revivification, involves the discharge of a battery into the body. To achieve the maximum affect of this form of supplementation of metabolic energy, the discharge is generally delivered, transcutaneously, to the site of the neuromuscular junction, also called the motor end plate region. Generally, conventional GS voltages can range from 10 to 100 volts DC, and the currents passed generally do not exceed 5 to 50 milliamperes. Both, the voltages and the currents, are delivered in pulsed form, in simulation of the way the nervous system delivers energy to post synaptic structures, whether they are organs or muscles. These pulses can be as brief as ¼ of a millisecond, and the frequency of pulses can be as high as 900 Hz.

IFC is essentially a deeper form of TENS. In normal operation, IFC modulates a high frequency (4000 Hz) carrier waveform with the same signal produced by a TENS unit. The high frequency carrier waveform penetrates the skin deeper than a regular TENS unit, with less user discomfort for a given level of stimulation. Once deep within the tissues, the carrier waveform is cancelled out, resulting in a TENS-like signal deep under the skin.

TENS units are commonly used at home for pain relief on a long-term basis. TENS units are generally pocket size. Most TENS units allow the user to adjust the intensity of the stimulation; some units also allow the user to select high-frequency stimulation 60-200 Hz or low-frequency stimulation 1-60 Hz. High frequency stimulation, sometimes called "conventional", is tolerable for hours, but the resultant pain relief lasts for a shorter period of time. Low-frequency stimulation, sometimes called "acupuncture-like", is slightly uncomfortable and tolerable for only 20-30 minutes, but the resultant pain relief lasts longer.

With specific reference to FIG. 1, the present disclosure provides a combined electro-stimulation and vibrational treatment (EVT) system 600. EVT system 600 incorporates vibration platform assembly 102, coupled to electro-stimulation assembly 402; both assemblies are controlled via unified controller 112. The components and function of the vibration platform assembly 102 are described above.

Electro-stimulation assembly 402 is equipped with a least one contact pad 408 configured for securing or attaching to the patient's body, e.g., leg, arm, chest, etc. Contact pad 408 may be coated with an adhesive appropriate for providing temporary adhesion of contact pad 408 to the patient's skin. Contact pad 408 transmits and applies electrical pulses produced by the electro-stimulation assembly 402 to localized points on the patient. In the case of multiple contact pads 408, unified controller 112 may be configured to individually control each contact pad 408 via one or more cables or wires 120a.

Both assemblies 102, 402 of the EVT system 600 are controlled by receiving signals from controller 112. Controller 112 includes a power supply for powering the assemblies 102, 402. Alternatively, each assembly can bes controlled by its own controller and/or power supply.

Electro-stimulation assembly 402 includes circuitry housed within member 114. In an alternative embodiment, electro-stimulation assembly 402 is housed within a housing other than member 114 and with or without operative communication with controller 112.

Figure 2B:
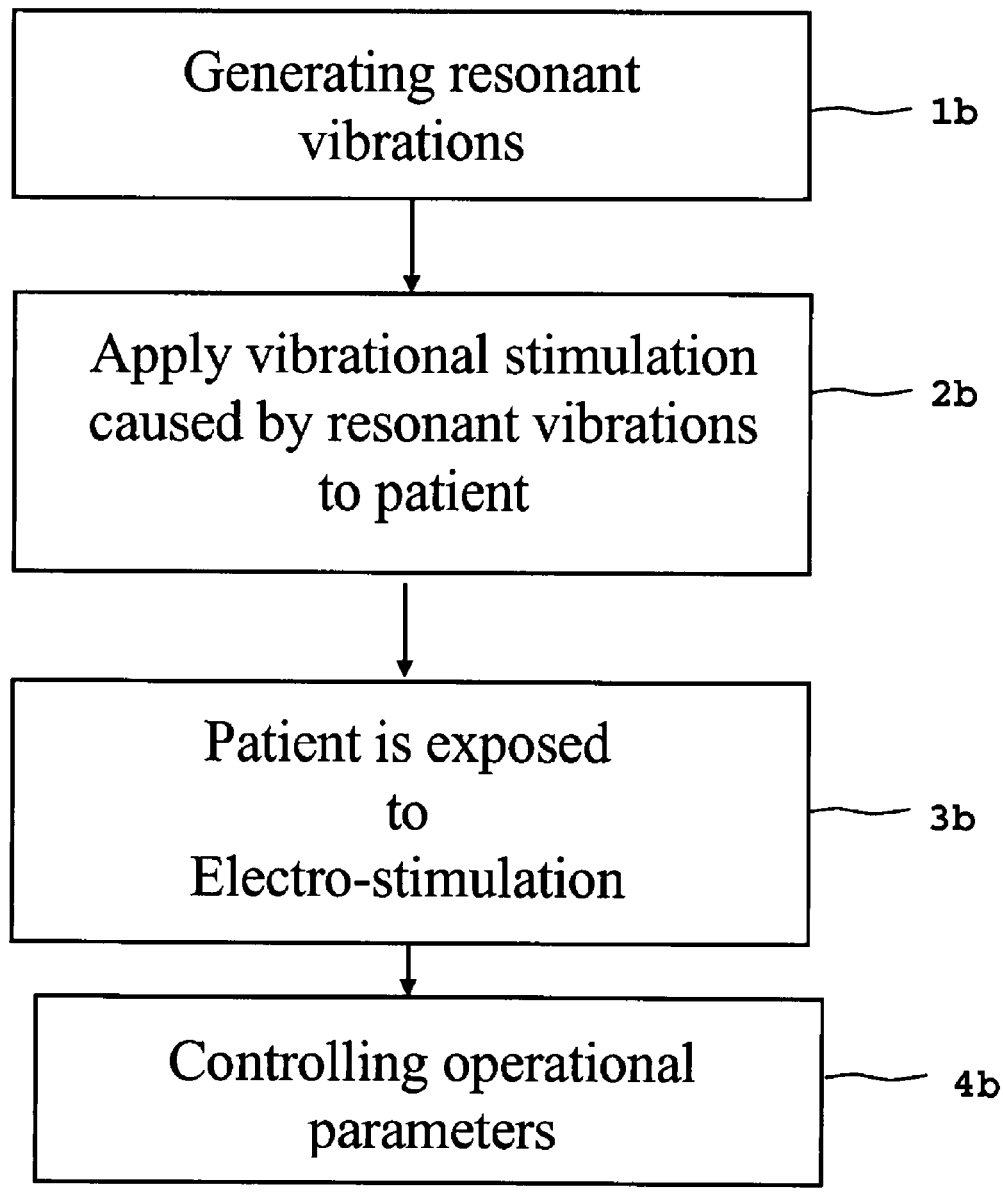
FIG. 2B is a flow chart illustrating an exemplary method for providing combined vibrational and electro-stimulation in accordance with the present disclosure.

With reference to FIGS. 1 and 2B, vibrational assembly 102 includes base 103 dimensioned to support and comfortably accommodate a patient in a standing position. Base 103 non-rigidly supports vibrational platform 104 of vibrational assembly 102, configured to impart or apply resonant vibrations to the musculoskeletal system of a patient's body. The vibrational assembly 102 generates resonant vibrations (Step 1b in FIG. 2B) having a frequency in the range of between 1 to 10 kHz. The resonant vibrations cause a vibrational stimulation. The vibrational stimulation is applied to the patient being supported by the platform 104 (Step 2b of FIG. 2B).

For patient stability and comfort, handrails 106 are provided; allowing the patient to easily remain in a proper posture and maintain balance while the vibration treatment is being administered. Additionally, a standing harness may be provided, aiding patients unable to stand on their own to maintain proper posture. The vibrational assembly 102 further includes a display 105 for displaying data, such as treatment data, as seen FIG. 1.

During vibrational treatment, electro-stimulation assembly 402 is actuated to generate electric pulses which are applied to the patient via one or more contact pads 408. The electric pulses cause electro-stimulation (Step 3b of FIG. 2B). Controller 112 controls the operational parameters of the EVT system 600 based on received signals from sensors positioned on the patient and/or within the electro-stimulation assembly 402 (Step 4b of FIG. 2B). By controlling the operational parameters, such as amplitude and frequency of the resonant vibrations and/or voltage and/or current of electric pulses, the level or intensity of the vibrational and/or electro-stimulation is changed.

The DMT system 200 and the electro-stimulation system 400 are, preferably, individually controllable such that a variety of treatment regimens may be devised. Additionally, a course of treatment may require alternating between the two therapeutic treatment systems for periods of time throughout the duration of a treatment session. For example, the vibrational assembly 102 may be operated for the full treatment session while the electro-stimulation assembly 402 is operated for 10-second periods during the treatment session. As a second example, the vibrational assembly 102 is operated for 20 minutes followed by operation of the electro-stimulation assembly 402 for 30 minutes. These are just two examples of the endless variations of timing sequences that are possible using the EVT system 600 of the present disclosure. The treatment session can be at least 10 minutes per day. The duration of the treatment can be 2-4 weeks.

Other treatment scenarios include having one or both assemblies (vibrational and electro-stimulation assemblies 102 and 402) operational or active during at least a portion of the treatment session, but at least one of the assemblies' operating parameters are adjusted manually or automatically during the treatment session or a portion thereof. The operating parameters can be adjusted independently of the other assemblies' operating parameters, or adjusted dependently, i.e., in accordance with, with changes in the operating parameter(s) of the other system.

Additionally, the assemblies 102, 402 of the present disclosure can be designed wherein an operating parameter of the first therapeutic treatment system changes in accordance with a change in an operating parameter of the second therapeutic treatment system (electro stimulation therapeutic treatment system 400). For example, during the treatment duration, the frequency of the vibrational assembly 102 can be increased by 5 Hz for each increase in the power output of the electro-stimulation assembly 402 of more than a predetermined wattage value. Therefore, an increase in the frequency of the vibrational assembly 102 depends on an increase in the power output of the electro-stimulation assembly 402.

It is contemplated that EVT system 600 can have one or more electro-stimulation assemblies 402. Each electro-stimulation assembly 402 can employ the same or different electrical modalities than the other assembly(ies) 402.

It is further envisioned that the electro-stimulation pulses generated by the electro-stimulation assembly 610 can be transmitted to contact pad 608 via any suitable known transmitting methods known in the available art, including, but not limited to cables, wires, and the likes. In one embodiment, electro-stimulation assembly 610 can be connected to contact pad via a cable 120a, as seen in FIG. 1.

As mentioned above, the first and second therapeutic treatment systems, 200 and 600, respectively, are controlled via the controller 112. In a preferred embodiment, controller 112 can be housed in front member 114. Member 114 can be of any suitable shape known in the available art. In addition, member 114 can have a plethora of different features. For example, member 114 can have a diagnostic panel that displays different operating parameters of the electro-stimulation assembly 402. Also, member 114 can have another diagnostic panel that displays different operating parameters of assembly 102. Member 114 can also be equipped with heart-rate displays, pulse-rate displays, calorie counter displays, fans and the likes. These features can be added or removed as needed. Furthermore, located on member 114 can be control switches, buttons and the like used for controlling both the electro-stimulation assembly 402 and the vibrational assembly 102.

Combined Electro-Stimulation, Ultrasound and Vibrational Therapeutic Treatment System The UVT system 100 and EVT system 600 are combined as shown in FIG. 1 to form an ultrasound, vibrational and electro-stimulation therapeutic treatment system 700. System 700 provides therapeutic treatment using a combination of ultrasound, vibrational and electro-stimulation. System 700 includes controller 112 configured for controlling vibrational assembly 102, ultrasound transducer assembly 110 and electro-stimulation assembly 402. Each assembly can be operated at any given time individually, or in conjunction with the operation of one or both of the other assemblies. As such, various treatment regimens can be devised to provide optimum therapeutic treatment to a patient using one or more of the assemblies of system 700 during a treatment session.

Additionally, a course of treatment may require alternating between the two or three of the therapeutic treatment systems 200, 300 and 600 for periods of time throughout the duration of a treatment session. For example, the vibrational assembly 102 may be operated for the full treatment session while the ultrasound transducer assembly 110 is operated for 10-second periods during the treatment session and the electro-stimulation assembly 402 is operated for 20-second periods during the treatment session. As a second example, the vibrational assembly 102 is operated for 20 minutes followed by operation of the ultrasound transducer assembly 110 for 30 minutes and followed by operation of the vibrational assembly 102 and electro-stimulation assembly 402 for 10 minutes. These are just two examples of the endless variations of timing sequences that are possible using system 700 of the present disclosure. The treatment session can be at least 10 minutes per day. The duration of the treatment can be 2-4 weeks.

Other treatment scenarios include having one, two or three assemblies operational or active during at least a portion of the treatment session, but at least one of the assemblies' operating parameters are adjusted manually or automatically during the treatment session or a portion thereof. The operating parameters can be adjusted independently of the other assemblies' operating parameters, or adjusted dependently, i.e., in accordance with, with changes in the operating parameter(s) of the other system.

Additionally, the assemblies of the present disclosure can be designed wherein an operating parameter of the first therapeutic treatment system changes in accordance with a change in an operating parameter of the second and/or third therapeutic treatment system. For example, during the treatment duration, the frequency of the vibrational assembly 102 can be increased by 5 Hz for each increase in the power output of the ultrasound transducer assembly 110 of more than a predetermined wattage value and/or an increase in the power output of the electro-stimulation assembly 402. Therefore, an increase in the frequency of the vibrational assembly 102 depends on an increase in the power output of the ultrasound transducer assembly 110 and/or electro-stimulation assembly 402. The three therapeutic treatment systems are controlled via the controller 112.

Figure 2C:
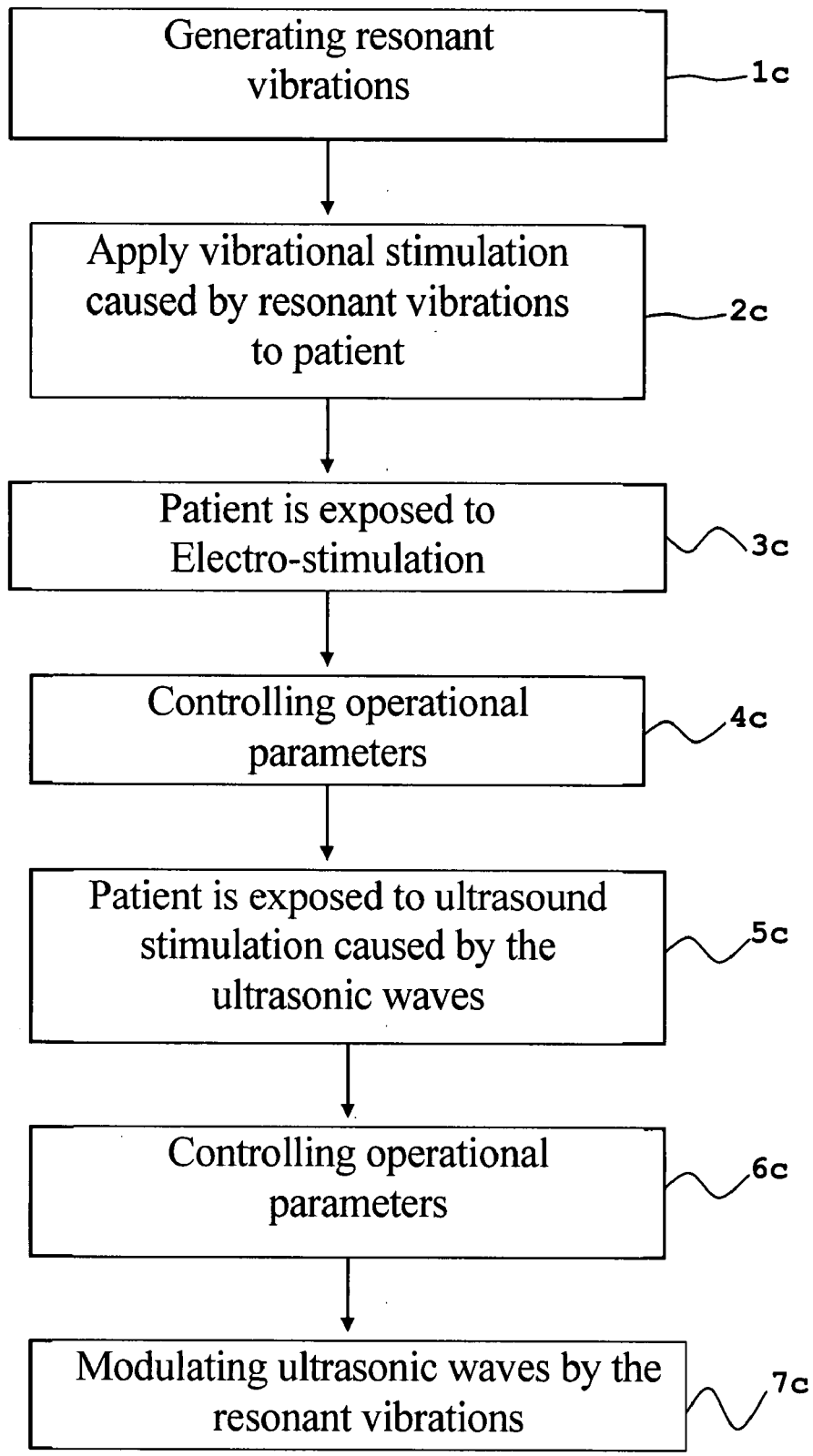
FIG. 2C is a flow chart illustrating an exemplary method for providing combined vibrational, elecro- and ultrasound stimulation in accordance with the present disclosure.

With reference to FIGS. 1 and 2C, vibrational assembly 102 includes base 103 dimensioned to support and comfortably accommodate a patient in a standing position. Base 103 non-rigidly supports vibrational platform 104 of vibrational assembly 102, configured to impart or apply resonant vibrations to the musculoskeletal system of a patient's body. The vibrational assembly 102 generates resonant vibrations (Step 1c in FIG. 2C) having a frequency in the range of between 1 to 10 kHz. The resonant vibrations cause a vibrational stimulation. The vibrational stimulation is applied to the patient being supported by the platform 104 (Step 2c of FIG. 2C).

For patient stability and comfort, handrails 106 are provided; allowing the patient to easily remain in a proper posture and maintain balance while the vibration treatment is being administered. Additionally, a standing harness may be provided, aiding patients unable to stand on their own to maintain proper posture. The vibrational assembly 102 further includes a display 105 for displaying data, such as treatment data, as seen FIG. 1.

During vibrational treatment, electro-stimulation assembly 402 is actuated to generate electric pulses which are applied to the patient via one or more contact pads 408. The electric pulses cause electro-stimulation (Step 3c of FIG. 2C). Controller 112 controls the operational parameters of system 700 based on received signals from sensors positioned on the patient and/or within the electro-stimulation assembly 402 (Step 4c of FIG. 2C).

The ultrasound transducer assembly 110 during treatment is also actuated, either simultaneously on non-simultaneously with one or both of the other two assemblies, to generate ultrasonic waves. The ultrasonic waves cause ultrasound stimulation. The ultrasound stimulation is applied to the patient supported by the platform (Step 5c of FIG. 2C). The controller 112 controls the operational parameters of the system 700 based on received signals from sensors positioned on the patient and/or within the ultrasound transducer assembly 110 (Step 6c of FIG. 2C). As described above, one of the key features of the present disclosure is that the resonant vibrations generated by the vibrational assembly 102 modulate the continuous ultrasonic waves generated by the ultrasound transducer assembly 110 (Step 7c of FIG. 2C) if both assemblies 102 and 110 are operational simultaneously.

The above examples are meant for illustrative purposes only, other combinations and treatment durations are contemplated and supported by the various embodiments of the present disclosure.

The described embodiments of the present disclosure are intended to be illustrative rather than restrictive, and are not intended to represent every embodiment of the present disclosure. Various modifications and variations can be made without departing from the spirit or scope of the present disclosure as set forth in the following claims both literally and in equivalents recognized in law.

What is claimed is:

1. A system having at least two therapeutic systems for providing therapeutic treatment to a patient, said system comprising:
   a first therapeutic treatment system comprising a non-rigidly supported platform configured to generate vibrations and to impart the generated vibrations to the patient;
   a second therapeutic treatment system configured to operate either alone or in conjunction with said first therapeutic treatment system during a treatment session, said second therapeutic treatment system being selected from at least one of an ultrasound therapeutic treatment system and an electro-stimulation therapeutic treatment system; and
   a controller configured to automatically change an operating parameter of the first therapeutic treatment system in accordance with a change in an operating parameter of the second therapeutic treatment system, wherein the operating parameter of the first therapeutic treatment system is the frequency of vibration of the platform, and the controller is configured to increase the frequency of vibration of the platform when the operating parameter of the second therapeutic system increases by more than a predetermined value.

2. The system of claim 1, wherein the operating parameter of the second therapeutic system is the power output of the second therapeutic system.

* * * * *